United States Patent
Plumptre

(10) Patent No.: US 9,399,099 B2
(45) Date of Patent: *Jul. 26, 2016

(54) DOSE SETTING MECHANISM FOR A DRUG DELIVERY DEVICE

(75) Inventor: David Plumptre, Worcestershire (GB)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 762 days.

This patent is subject to a terminal disclaimer.

(21) Appl. No.: 13/321,313

(22) PCT Filed: May 28, 2010

(86) PCT No.: PCT/EP2010/057489
§ 371 (c)(1),
(2), (4) Date: Mar. 12, 2012

(87) PCT Pub. No.: WO2010/139642
PCT Pub. Date: Dec. 9, 2010

(65) Prior Publication Data
US 2012/0165748 A1    Jun. 28, 2012

Related U.S. Application Data

(60) Provisional application No. 61/182,853, filed on Jun. 1, 2009.

(30) Foreign Application Priority Data

Jul. 10, 2009  (EP) .................................. 09009045

(51) Int. Cl.
| A61M 5/315 | (2006.01) |
| A61M 5/24 | (2006.01) |
| A61M 5/34 | (2006.01) |
| A61M 5/31 | (2006.01) |

(52) U.S. Cl.
CPC ............. *A61M 5/31551* (2013.01); *A61M 5/24* (2013.01); *A61M 5/31535* (2013.01); *A61M 5/31548* (2013.01); *A61M 5/31561* (2013.01); *A61M 5/347* (2013.01); *A61M 5/348* (2013.01); *A61M 2005/2407* (2013.01); *A61M 2005/3104* (2013.01); *Y10T 29/49826* (2015.01)

(58) Field of Classification Search
CPC ............ A61M 5/3155; A61M 5/3157; A61M 5/31528; A61M 5/31563; A61M 5/31541; A61M 2005/3154; A61M 5/31551
See application file for complete search history.

(56) References Cited

U.S. PATENT DOCUMENTS

| 6,221,046 B1* | 4/2001 | Burroughs et al. ............ 604/153 |
| 7,094,221 B2* | 8/2006 | Veasey et al. ................. 604/187 |
| 2009/0012479 A1* | 1/2009 | Moller et al. ................. 604/211 |
| 2012/0165743 A1* | 6/2012 | Jones ........................... 604/189 |

FOREIGN PATENT DOCUMENTS

| WO | 2004/078242 | 9/2004 |
| WO | 2006/024461 | 3/2006 |
| WO | 2006/079481 | 8/2006 |

OTHER PUBLICATIONS

International Search Report and Written Opinion for International App. No. PCT/EP2010/057489, mailed Sep. 6, 2010.
International Preliminary Report of Patentability for International App. No. PCT/EP2010/057489, completed Aug. 11, 2011.

* cited by examiner

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

A dose setting mechanism of a drug delivery device and a respective method of assembling said dose setting mechanism. The dose setting mechanism includes an inner housing having a helical groove along an external surface of the housing. The inner housing includes a rotational stop member near one end of the helical groove. The dose setting mechanism also includes a dial sleeve rotatably engaged with the helical groove of the inner housing. When a user rotates the dial sleeve to select a dose, the rotational stop member prevents the user from selecting a dose greater than a pre-defined maximum selectable dose.

11 Claims, 3 Drawing Sheets

DOSE SETTING MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/057489 filed May 28, 2010, which claims priority to U.S. Provisional Patent Application No. 61/182,853 filed on Jun. 1, 2009 and European Patent Application No. 09009045.7 filed on Jul. 10, 2009. The entire disclosure contents of these applications are herewith incorporated by reference into the present application.

FIELD OF THE INVENTION

The present application is generally directed to dose setting mechanisms for drug delivery devices. More particularly, the present application is generally directed to dose setting mechanisms comprising an inner housing and a dial sleeve and used for drug delivery devices. Aspects of the invention may be equally applicable in other scenarios as well.

BACKGROUND

Pen type drug delivery devices have application where regular injection by persons without formal medical training occurs. This may be increasingly common among patients having diabetes where self-treatment enables such patients to conduct effective management of their disease.

There are basically two types of pen type delivery devices: resettable devices (i.e., reusable) and non-resettable (i.e., disposable). These types of pen delivery devices (so named because they often resemble an enlarged fountain pen) are generally comprised of three primary elements: (i) a cartridge section that includes a cartridge often contained within a housing or holder; (ii) a needle assembly connected to one end of the cartridge section; and (iii) a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then a dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle contained within the dose setting mechanism presses against the bung or stopper of the cartridge. This force causes the medication contained within the cartridge to be injected through the attached needle assembly. After an injection, as generally recommended by most drug delivery device and/or needle assembly manufacturers and suppliers, the needle assembly is removed and discarded.

The dose setting mechanism further comprises a number sleeve which is used to display the dialled dose. This number sleeve has dose numbers on the external surface so that the dose number dialled is visible through a window, aperture or lens in the housing. The number sleeve must be prevented from being dialled out beyond a pre-set rotational stop distance so that it does not disengage from the housing.

It is therefore an object of the present invention to provide a dose setting mechanism which meets above mentioned needs. It is another object of the present invention to specify a easy and cost-effective method of assembling such dose setting mechanism.

SUMMARY

The above object is solved by a dose setting mechanism for a drug delivery device comprises an inner housing having a helical groove, which is preferably a male helical groove, along an external surface of the inner housing and a dial sleeve rotatably engaged with the helical groove of the inner housing. The inner housing comprises a first rotational stop member near one end of the helical groove. When a user rotates the dial sleeve to select a dose, the first rotational stop member prevents the user from selecting a dose greater than a pre-defined maximum selectable dose.

The dose dial sleeve may include an inner surface having a helical groove, which is preferable a male helical groove, and a second rotational stop member. The first rotational stop member may mate with the second rotational stop member when a user attempts to select a dose greater than the pre-defined maximum selectable dose.

The above object is further solved by a method of assembling a drug delivery dose setting mechanism. According to an exemplary arrangement, the method includes establishing a helical groove along an outer surface of an inner housing. The method further includes defining at least one rotational stop feature near one end of the helical groove. The rotational stop feature may reside along the outer surface of the inner housing. The method further includes assembling a dial sleeve over the inner housing by rotating the dial sleeve with respect to the inner housing, where the dial sleeve is in a threaded engagement with the helical groove on the inner housing.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
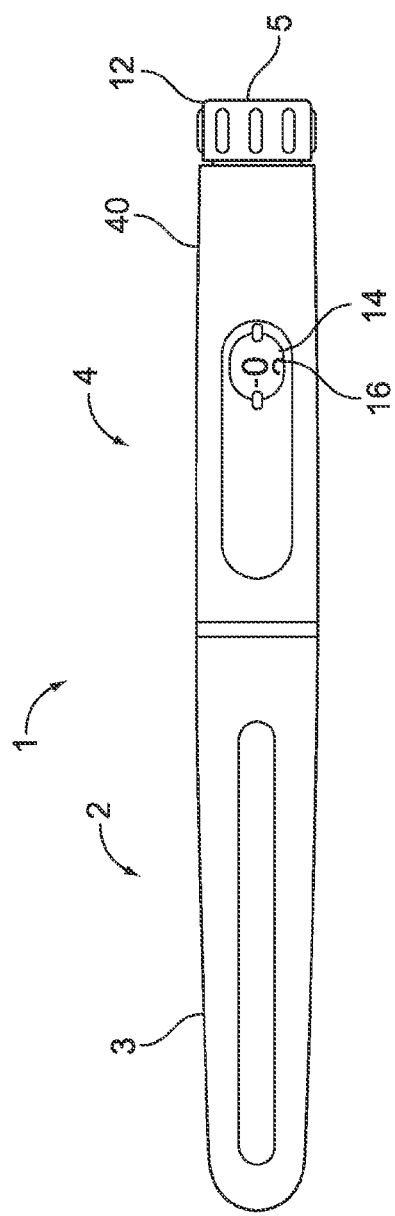
FIG. 1 illustrates an embodiment of a drug delivery device comprising the inventive dose setting mechanism.

The terms "medicinal product" or "drug" or "medicament" or "medication", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (AC S), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Referring to FIG. 1, there is shown a drug delivery device 1 in accordance with a first arrangement of the present invention. The drug delivery device 1 comprises a housing having a cartridge retaining means 2, and dose setting mechanism 4. A first end of the cartridge retaining means 2 and a second end of the dose setting mechanism 4 are secured together by retaining features. In this illustrated arrangement, the cartridge retaining means 2 is secured within the second end of the dose setting mechanism 4. A removable cap 3 is releasably retained over a second end or distal end of a cartridge retaining means 2. As will be described in greater detail, the dose setting mechanism 4 comprises a dose dial grip 12 and a window or lens 14. To set a dose of medication contained within the drug delivery device 1, a user rotates the dose dial grip 12 and the window 14 allows a user to view the dialled dose by way of a dose scale arrangement 16.

Figure 2:
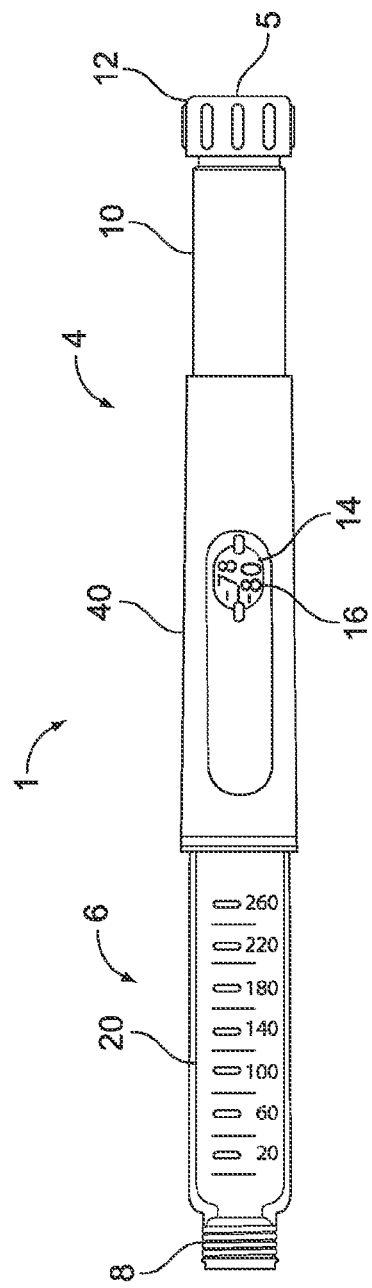
FIG. 2 illustrates the embodiment of the drug delivery device illustrated in FIG. 1 with a cap removed and showing a cartridge housing containing a cartridge.

FIG. 2 illustrates the medical delivery device 1 of FIG. 1 with the cover 3 removed from the distal end of the medical delivery device 1. As illustrated, a cartridge 20 from which a number of doses of a medicinal product may be dispensed is provided in the cartridge housing 6. Preferably, the cartridge 20 contains a type of medicament that must be administered often, such as once or more times a day. Once such medicament is insulin. A bung or stopper (not illustrated in FIG. 2) is retained in a first end or a proximal end of the cartridge 20.

The dose setting mechanism 4 of the drug delivery device illustrated in FIG. 2 may be utilized as a reusable (and hence resettable) or a non-reusable (and hence non-resettable) drug delivery device. Where the drug delivery device 1 comprises a reusable drug delivery device, the cartridge is removable from the cartridge housing 6. The cartridge 20 may be removed from the device without destroying the device but merely by the user disconnecting the dose setting mechanism 4 from the cartridge holder 20.

In use, once the removable cap 3 is removed, a user can attach a suitable needle assembly to the distal end 8 of the cartridge housing 6. Such needle unit may be screwed onto a distal end 8 of the housing 6 or alternatively may be snapped onto this distal end. A replaceable cap 3 is used to cover the cartridge housing 6 extending from the dose setting mechanism 4. Preferably, the outer dimensions of the replaceable cap 3 are similar or identical to the outer dimensions of the dose setting mechanism 4 so as to provide an impression of a unitary whole when the replaceable cap 3 is in position covering the cartridge holder 2.

Returning to FIGS. 1-2, a dose dial grip 12 is disposed about an outer surface of the second end of the dial sleeve 10, which may be a number sleeve. An outer diameter of the dose dial grip 12 preferably corresponds to the outer diameter of the outer housing 40. The dose dial grip 12 is secured to the dial sleeve 10 to prevent relative movement between these two components. In one preferred arrangement, the dose dial grip 12 and number sleeve 10 comprise a one piece component that is rotationally coupled to a clutch and drive sleeve and axially coupled to the number sleeve 10. However, alternative coupling arrangements may also be used.

In normal use, the operation of the dose setting mechanism 4 generally occurs as follows. To dial a dose in the arrangement illustrated in FIGS. 1-2, a user rotates the dose dial grip 12. A user may rotate the dose dial grip towards the user to set a dose. Alternatively, a user may rotate the dose dial grip away from the user to set a dose. A driver, clutch and the dial sleeve 10 rotate along with the dose dial grip 12. The dial sleeve 10 extends in a proximal direction away from the outer housing 40. In this manner, the driver climbs a spindle. The dial sleeve 10 may extend in a proximal direction away from the housing until a user sets a maximum selectable dose.

FIG. 2 illustrates the medical delivery device after a desired dose of for example 79 International Units (IU) has been dialled. When this desired dose has been dialled, the user may then dispense the desired dose of 79 IU by depressing the button 5. As the user depresses the button 5, this displaces the clutch axially with respect to the dial sleeve 10, causing the clutch to disengage. However the clutch remains keyed in rotation to the driver. The dial sleeve 10 and associated dose dial grip 12 are now free to rotate. The driver is prevented from rotating with respect to the outer housing 40 but it is free to move axially with respect thereto. The longitudinal axial movement of the driver causes the spindle to rotate and thereby to advance the bung (piston) in the cartridge 20.

The dose setting mechanism in accordance with embodiments of the invention prevents a user from selecting a dose greater than a pre-defined maximum selectable dose. Components of the dose setting mechanism in accordance with embodiments are described in greater detail with reference to FIGS. 3-6.

Figure 3:
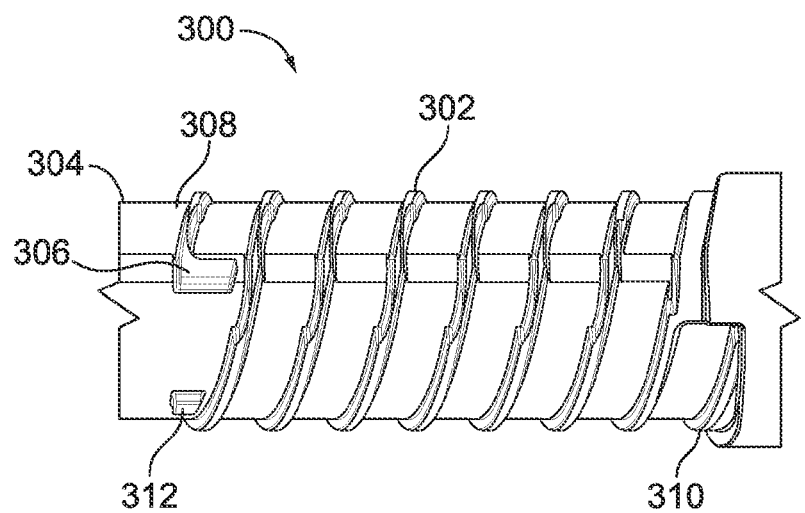
FIG. 3 illustrates a partial view of an embodiment of an inner housing of the drug delivery device illustrated in FIG. 1.

FIG. 3 illustrates a partial view of an inner housing 300 of the dose setting mechanism 4. As depicted, the inner housing 300 has a helical groove 302 along the external surface 304 of the inner housing 300. The helical groove 302 is preferably a male helical groove, i.e. a thread. Alternatively, the helical groove 302 may be a female groove or some other equivalent groove structure.

The inner housing 300 also includes a rotational stop member 306 near one end of the helical groove 302. The helical groove comprises a proximal end 308 and a distal end 310. Preferably, the rotational stop member 306 is located near the proximal end 308 of the helical groove 302. Alternatively, the rotational stop member 306 may be moulded on a flexible arm or a similar bendable element. Moulding the rotational stop member 306 on a flexible arm may aid in the assembly of the dose setting mechanism, which is described in more detail below. In both embodiments the rotational stop member 306 comprises a cuboid-like projection projecting outwardly in radial direction from the external surface 304 of the inner housing 300 and having a certain dimension in axial direction of the inner housing 300 as shown in FIG. 3. The projection further forms a face running approximately perpendicular to the longitudinal direction of the helical groove 302 for abutment with the rotational stop member 406 of the dial sleeve 10.

Figure 4:
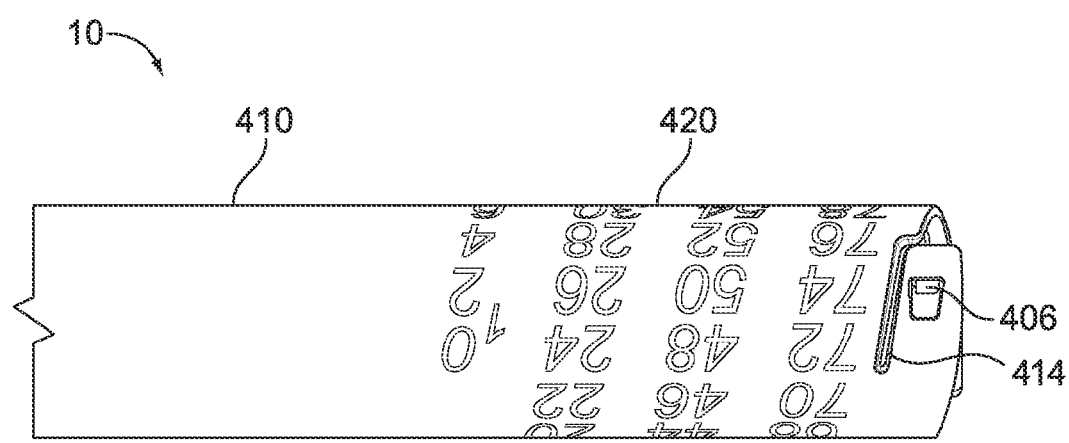
FIG. 4 illustrates an embodiment of a dial sleeve of the drug delivery device illustrated in FIG. 1.
Figure 5:
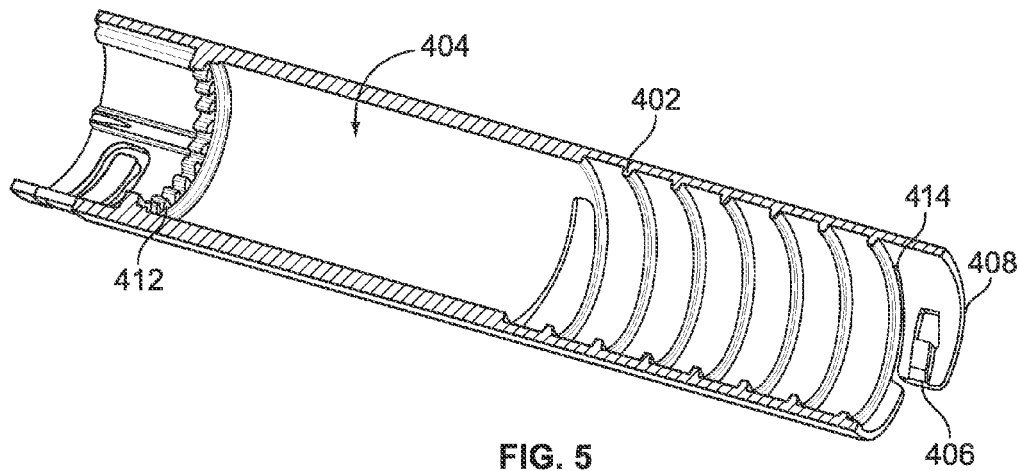
FIG. 5 illustrates a half sectional view of the dial sleeve illustrated in FIG. 4.

FIG. 4 illustrates the dial sleeve 10 of the dose setting mechanism 4. As shown, the dial sleeve 10 is preferably a number sleeve. As is known in the art, the number sleeve may operate to indicate to the user the amount of dose dialled. When the dose setting mechanism is assembled, the dial sleeve 10 is assembled over the inner housing 300. The dial sleeve 10 is capable of rotatably engaging with the helical groove 302 of the inner housing 300. As depicted in FIG. 5, for it the dial sleeve 10 includes a helical groove 402 on the internal surface 404 of the dial sleeve 10. The dial sleeve 10 further includes a rotational stop member 406 comprising a cuboid-like projection projecting inwardly from the internal surface 404 of the dial sleeve 10. The projection has further a certain dimension in axial direction of the dial sleeve 10 and forms a face running approximately perpendicular to the longitudinal direction of the helical groove 402 for abutment with the rotational stop member 306 of the inner housing 300. Preferably, the helical groove 402 is a male groove, i.e. a thread. Alternatively, the helical groove 402 may be a female groove or some other equivalent groove structure.

In an exemplary arrangement, the inner housing 300 also includes a guide lug 312 on the external surface. Preferably, the guide lug 312 may constrain the helical thread 402 form on the dial sleeve 10. When the dial sleeve 10 is disposed over the inner housing 300, helical groove 402 may engage with the helical groove 302 and the guide lug 312 of the inner housing 300.

When a user of the drug delivery device 1 rotates the dose dial grip 12 of the inventive dose setting mechanism 4, the first rotational stop member 306 prevents the user from selecting a dose greater than a pre-defined selectable dose, such as a pre-defined maximum selectable dose. Specifically, the first rotational stop member 306 of the inner housing may mate or engage with the second rotational stop member 406 of the dial sleeve 10 when a user attempts to select a dose greater than the pre-defined maximum selectable dose. In detail, two opposite faces of the rotational stop members 306, 406 described above abut and therefore prevent movement of the dial sleeve 10 when a user attempts to select a dose greater then the maximum selectable dose. Rotational stop members 306 and 406 may have complementary undercuts that strengthen the engagement between the two features. The pre-determined maximum selectable dose may be, for example, 80 units. Other pre-defined maximum selectable doses are possible as well.

In an preferred embodiment the rotational stop feature 406 may be on a flexible arm 408 which is separated from the remaining part of the dial sleeve 10 by a cutting slit 414 as shown in FIGS. 4 and 5. The flexible arm 408 allows the dial sleeve 10 to be easily assembled over the inner housing 300, and this assembly is discussed in greater detail below.

In an exemplary arrangement, the dial sleeve 10 may also comprise teeth-like clutch features 412 on the internal surface 404. The internal clutch features 412 restrict the design options for de-moulding the part. As an example, the clutch features 412 can engage similar features on a drive sleeve so that the number sleeve and drive sleeve rotate together when setting a dose. However, the clutch features 412 disengage when dispensing a dose so as to allow relative rotation. It is advantageous if the groove form 402 on the inner surface 404 of the number sleeve 10 can be moulded with an axially moving core pin so as to simplify the mould tool actuation. This can be achieved if the inner groove form 402 comprises less than one turn and the rotational stop feature 406 is moulded as a rib extending proximally from one end of the groove form 402 with the an equivalent internal diameter to this groove form. In this manner, the dose dial sleeve 10 can run in the groove between the helical groove 302 on the inner housing. However, the presence of the internal clutch features 412 prevents a core pin from extending proximally out of the part. Consequently, the internal surfaces distal to these clutch features have to be moulded with a rotating core pin extending distally from the part.

The dose setting mechanism 4 may also comprise an outer housing 40 that may house the inner housing 300 and the dial sleeve 10 when the dose setting mechanism is assembled. The outer housing 40 preferably has an internal diameter that is equal to or substantially equal to the outer diameter of the dial sleeve 10. Therefore, when the dose setting mechanism is assembled, the outer housing 40 has an internal diameter which defines a clearance fit to the outside diameter of the dial sleeve 10. This clearance fit prevents the flexible rotational stop member 406 on the dial sleeve 10 from disengaging from the rotational stop member 306 on the inner housing 300 when the user attempts to dial beyond the maximum dose stop.

Figure 6:
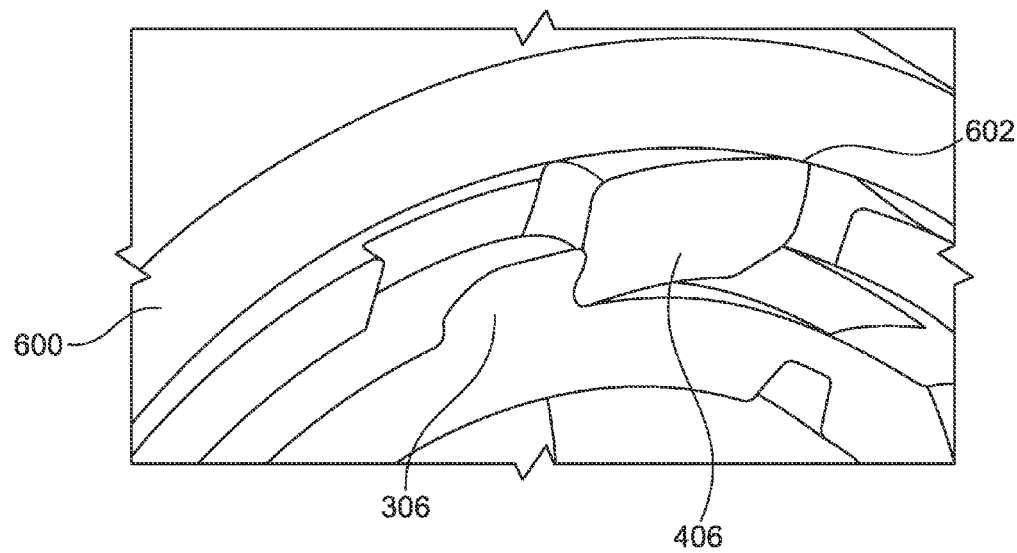
FIG. 6 illustrates a cross sectional view of the inner housing of FIG. 3 engaged with the dial sleeve of FIGS. 4 to 5.

FIG. 6 depicts how an exemplary outer housing 600 preventing disengagement of the rotational stop members 306 and 406. As depicted, the rotational stop member 306 engages with the rotational stop member 406 when a user dials the maximum selectable dose. Due to this engagement, the user is prevented from dialling a dose greater than the maximum selectable dose. Under a load, the flexible arm 408 rotates out and contacts the inside surface of the outer housing 600 at point 602, which prevents disengagement of the rotational stop member 306 from the inner housing stop member 406. Without the outer housing 600 contacting the rotational stop member 406, the rotational stop member 406 could disengage from rotational stop member 306 under heavy load.

The components described in reference to FIGS. 3-6 can be assembled in order to provide a drug delivery dose setting mechanism, such as dose setting mechanism 4. The dial sleeve 10 may be assembled over the inner housing 300 by rotating the dial sleeve 10 with respect to the inner housing 300. As mentioned above, the dial sleeve 10 preferably includes a helical groove 402 that is capable of engaging with the helical groove 302 of the inner housing 300. Further, a rotational stop feature 406 may be provided along the inner surface 404 of the dial sleeve 10, as described above.

During the assembly of the dose setting mechanism, the dial sleeve 10 may be assembled over the inner housing 300, following a helical path during assembly while engaging with the external thread (i.e., the helical groove) on the inner housing 300. Due to rotational stop member 406 being disposed on the flexible arm 408 and/or rotational stop member 306 being disposed on a flexible arm, the rotational stop members 306 and 406 may pass over one another during assembly. The rotational stop members 306 and 406 may snap over each other during assembly of the dial sleeve over the inner housing. This snapping may occur due to the flexibility of the flexible arm 408 or the flexibility of the rotational stop member 306 (or both) and the absence of the outer housing 600. While the flexible arm or arms allow rotational stops 306 and 406 to pass over one another during assembly, the design of the flexible arms does not allow the rotational stops 306 and 406 to pass over one another when a user dials a dose. Rather, when a user tries to rotate the dial sleeve 10 back out along the helical path 302 by more than the predefined maximum selectable dose, the rotational stop members 306, 406 engage one another.

The rotational stop members 306 and 406 may be further prevented from disengagement when the outer housing 600 is assembled over the dial sleeve 10. During the assembly of the dose setting mechanism, the outer housing 600 may be provided over the inner housing 300 and the dial sleeve 10. As mentioned above, the outer housing 600 has an internal diameter, and, when the outer housing 600 is provided over the dial sleeve 10, this internal diameter may be utilized to prevent the rotational stop member 406 of the dose dial sleeve 10 from disengaging the rotational stop member 306 of the inner housing 300.

In a preferred arrangement, the dose setting mechanism 4 is preferably coupled to a cartridge housing 6, as depicted in FIGS. 1 and 2. The dose setting mechanism 4 may be permanently coupled to the cartridge housing 6.

Advantageously, the inner housing 300 enables the dial sleeve (number sleeve) 10 to be provided with a helical groove 402 on an inner surface 404 of the dial sleeve 10, rather than providing such a helical groove on an external surface 410 of the dial sleeve 10. Providing such an internal groove 402 results in a number of advantages. For example, this results in the advantage of providing more surface area along the outer surface 410 of dial sleeve 10 so as to provide the scale arrangement 420. More number dial surface area may be used for drug or device identification purposes.

Having the groove 402 on the inside of the dial sleeve 10 maximizes the area for the dose numbers and minimizes the effective diameter of the groove engagement to the inner housing, thus reducing the risk of this groove interface jamming during dispensing by increasing the effective groove helix angle.

Another advantage of providing the helical groove 402 on the inner surface 404 of the dial sleeve 10 is that this inner groove 402 is now protected from dirt ingress. In other words, it is more difficult for dirt to become logged in this inner groove interface than if the groove were provided along the outer surface 410 of the number sleeve 10. This feature is particularly important for a re-settable drug delivery device which will have to function over a much longer period of time compared to a non-resettable device.

The effective driving diameter of the grooved interface between the number sleeve 10 and the inner housing 300 is reduced compared to certain known drug delivery devices for the same outer body diameter. This improves efficiency and enables the drug delivery device to function with a lower pitch for this grooves 302, 402 and groove guide connection. In other words, as the helix angle of the thread determines whether when pushed axially, the number sleeve will rotate or lock to the inner body wherein this helix angle is proportional to the ratio of pitch/effective driving diameter. Because the dial sleeve 10 has the helical groove 402 on the internal surface 404 of the dial sleeve, the outer surface 410 may be a generally smooth outer surface.

By utilizing the inner housing 300 and the dial sleeve 10, the dose setting mechanism 4 results in certain manufacturing advantages as well. For example, in one preferred arrangement, the dial sleeve 10 may be moulded as a single component. The design of the dial sleeve 10 in accordance with embodiments allows the dial sleeve 10 to be moulded as a single component. Moulding the dial sleeve 10 as a single component may beneficially lower manufacturing and/or assembly costs.

Another advantage of a dose setting mechanism in accordance with this arrangement is that the dose setting mechanism 4 has a reduced number of components over other known dose setting mechanisms In other words, the dial sleeve 10 is a single component having the clutch features 412, the inner groove 402 mating with the outer groove 302 on the inner housing 300 and the maximum dose stop features 306, 406 acting between these two parts.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for a drug delivery device, said mechanism comprising:
   an inner housing having a helical groove along an external surface of said inner housing, where the external surface defines a tube having a circular cross-section and said inner housing comprising a first rotational stop member near one end of said helical groove, where the first rotational stop is cuboid-like projection projecting radially outward from the external surface;
   a dial sleeve rotatably engaged with said helical groove of said inner housing such that the dial sleeve is assembled over the inner housing and rotates relative to the inner housing, said dial sleeve comprises a generally smooth outer surface and an inner surface having a helical groove and a second rotational stop member; and
   an outer housing that houses both the dial sleeve and the inner housing;
   wherein, said first rotational stop member is configured to prevent a user from selecting a dose greater than a predefined maximum selectable dose when said user rotates said dial sleeve to select a dose;
   wherein said first rotational stop member engages with said second rotational stop member of said dial sleeve when a user attempts to select a dose greater than said predefined maximum selectable dose and
   wherein said second rotational stop member comprises a flexible member and is configured to pass over the first rotational stop when the dial sleeve is assembled over the inner housing.

2. The dose setting mechanism of claim 1 wherein said first rotational stop member comprises a flexible arm member.

3. The dose setting mechanism of claim 1 wherein said one end of said helical groove of said inner housing comprises a proximal end of said helical groove.

4. The dose setting mechanism of claim 1 wherein said dose setting mechanism is capable of permanently coupling to a cartridge housing which comprises a removable cartridge.

5. The dose setting mechanism of claim 1 wherein said dial sleeve is capable of rotating towards a user to set a dose, by using a dose dial grip.

6. A drug delivery device comprising a dose setting mechanism according to claim 1 and a cartridge of medication.

7. The dose setting mechanism of claim 1 wherein the flexible member of the second rotational member is separated from part of the dial sleeve by a cutting slit.

8. The dose setting mechanism of claim 1 wherein the flexible member of the second rotational member has a projection comprising a face that is configured to engage the first rotational stop member.

9. The dose setting mechanism of claim 2 wherein the flexible arm member of the first rotational member has a projection comprising a face that is configured to engage the second rotational stop member.

10. The dose setting mechanism of claim 1 wherein the flexible member of the second rotational member has a projection comprising a first face and the first rotational stop member comprises a flexible arm member having a projection comprising a second face, where the first and second faces are configured to engage each other to prevent rotation of the dial sleeve greater than a pre-defined maximum selectable dose.

11. The dose setting mechanism of claim 1 further characterized in that the cuboid-like projection comprises a wedge-shaped structure with at least one undercut configured to engage the second rotational stop.

* * * * *